United States Patent [19]

Ishimoto et al.

[11] 4,138,553

[45] Feb. 6, 1979

[54] 3-METHYLENE CEPHALOSPORANIC ACID DERIVATIVES AND PROCESS FOR PREPARATION THEREOF

[75] Inventors: Sachio Ishimoto, Tokyo; Hisao Yamaguchi, Hino; Yoshinori Kato, Hino; Takeo Oba, Hino; Kenji Ozawa, Hino; Yataro Ichikawa, Fuchu; Koji Nakagawa, Iwakuni; Hideki Tsuruta, Hino, all of Japan

[73] Assignee: Teijin Limited, Osaka, Japan

[21] Appl. No.: 841,321

[22] Filed: Oct. 11, 1977

Related U.S. Application Data

[62] Division of Ser. No. 741,021, Nov. 11, 1976, abandoned.

[51] Int. Cl.$^2$ ............................................. C07D 501/02
[52] U.S. Cl. ................................. 544/18; 260/239.1; 544/27; 544/28
[58] Field of Search .......................................... 544/18

[56] References Cited

U.S. PATENT DOCUMENTS

| | | | |
|---|---|---|---|
| 3,852,295 | 12/1974 | Graham et al. | 544/18 |
| 3,879,398 | 4/1975 | Ellerton et al. | 544/18 |
| 3,966,720 | 1/1976 | Tomioka et al. | 544/18 |
| 4,075,203 | 2/1978 | Chos | 544/18 |

Primary Examiner—Nicholas S. Rizzo
Attorney, Agent, or Firm—Wenderoth, Lind & Ponack

[57] ABSTRACT

Novel substituted hydrazide derivatives of 7-(substituted)amino-3-methylene-cepham-4-carboxylic acids expressed by the formula

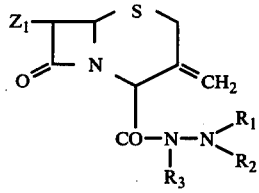

wherein $R_1$ represents alkyl containing at least 3 carbon atoms, cycloalkyl, or optionally substituted aryl, and one of $R_2$ and $R_3$ represents hydrogen with the other being hydrogen or the same as $R_1$; or $R_1$ and $R_2$ form a heterocyclic ring optionally through a hetero atom together with the attached nitrogen and $R_3$ represents hydrogen atom; and $Z_1$ represents amino or protected amino; and acid addition salts thereof, which are useful as intermediates for synthesizing cephalosporin antibiotics. These compounds can be prepared in high yields from the corresponding substituted hydrazide derivatives of 6-substituted amino-1-oxide-2, 2-dimethylpenam-3-carboxylic acids, which are readily available at low costs, by heating them in the presence of a thermal rearrangement promotor such as organic sulfonic acids and optionally in the further presence of a tertiary nitrogen-containing cyclic compound, followed if desired by splitting off the amino-protecting group and converting the product to acid addition salts.

13 Claims, No Drawings

3-METHYLENE CEPHALOSPORANIC ACID DERIVATIVES AND PROCESS FOR PREPARATION THEREOF

This application is a division of application Ser. No. 741,021, filed Nov. 11, 1976, now abandoned.

This invention relates to novel cephalosporanic acid derivatives, and more specifically, to substituted hydrazide derivatives of 7-(substituted)amino-3-methylene-cepham-4-carboxylic acids, and a process for preparing these derivatives.

Since 3-methylene-cepham-4-carboxylic acid derivatives contain an active methylene group at the position of the cepham ring, they are useful as intermediates for the synthesis of cephalosporin antibiotics.

Some methods have already been suggested for the synthesis of these intermediates. The prior methods include, for example, the electrolysis of 3-acetoxymethyl-7-amino-3-cepham-4-carboxylic acid or 3-acetoxymethyl-7-acylamide-3-cepham-4-carboxylic acid or its salts [M. Ochiai et al., Tetrahedron Letters (23) 2341–2344 (1972)]; the reduction of 3-acetoxymethyl-7-acylamide-3-cephem-4-carboxylic acid with chromium (II) salts [M. Ochiai et al., Journal of the Chemical Society, Chemical Communications, 800 (1972)]; the reduction of 3-substituted-thiomethyl-7-amino-3-cephem-4-carboxylic acid, 3-substituted-thiomethyl-7-acylamide-3-cephem-4-carboxylic acid, or its ester with Raney nickel or zincformic acid [R. R. Chauvette et al., The Journal of Organic Chemistry, 38 (17), 2994–2999 (1973)]; and the reduction of 7-amino-3-acetoxymethyl-3-cephem-4-carboxylic acid, its oxide, or salts of these with a metal having a standard potential of $-2.4$ to $-0.4$ volt or its amalgam at a pH of 1 to 8 in the presence of water [West German Laid-Open Specification No. 2400067]. However, because the cephalosporin derivatives used as starting materials are prepared from cephalosporin C which is produced by an expensive biological process with rather low productivity, these prior methods have the disadvantage that very expensive starting materials must be used.

Very recently, a method was suggested for preparing 3-methylene-cepham-4-carboxylic acid esters of the following formula

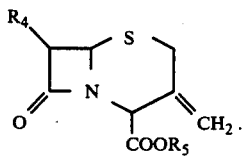

wherein $R_4$ represents an amino group or a substituted amino group, and $R_5$ represents an ester residue, which comprises the thermal rearrangement of a penicillin-1-oxide of the following formula

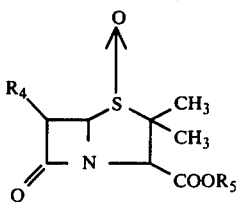

wherein $R_4$ and $R_5$ are the same as defined above, in the presence of a certain kind of phosphorus compound (Japanese Laid-Open Patent Publication No. 111092/75). This method shows an advance over the known methods in that it starts from penicillin derivatives which are readily available at low costs. Tracing of this method by the present inventors, however, showed that the 3-methylene-cepham-4-carboxylic acid esters are obtained usually in a very low yield of less than 7%, and the process is far from satisfactory for commercial practice.

In connection with the thermal rearrangement of penicillin-1-oxide, D. H. R. Barton et al. reported that methyl 7β-phenylacetamide-3-methylceph-3-em-4-carboxylate having a 3,4-double bond of the following formula

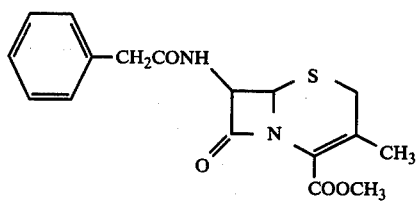

was obtained by heating (1S)-N-6β-phenylacetamidopenicillanoyl-N,N'-di-isopropyl hydrazine S-oxide of the formula

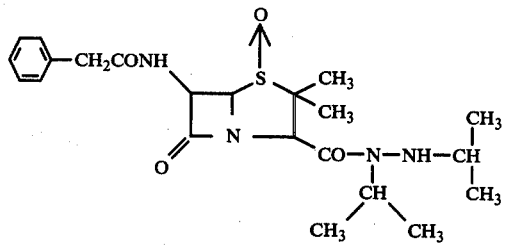

in anhydrous dioxane containing pyridine and orthophosphoric acid under reflux for 18 hours, oxidatively cleaving the hydrazide group of the reaction product, and then esterifying the product.

We have now found that when a substituted hydrazide derivative of 6-substituted amino-1-oxide-2,2-dimethyl-penam-3-carboxylic acid is heated in the presence of a certain organic acid or its derivative, such as organic sulfonic acids, mono- or di-esters of phosphoric acid, organic phosphonic acids, or monoesters thereof in an inert solvent, a thermal rearrangement reaction takes place and a novel substituted hydrazide derivative of 7-substituted amino-3-methylene-cepham-4-carboxylic acid containing a 3-methylene group not disclosed in the Barton et al. report cited above is formed in good yields.

It is an object of this invention to provide novel substituted hydrazide derivatives of 7-(substituted) amino-3-methylene-cepham-4-carboxylic acids.

Another object of this invention is to provide a process for preparing the novel substituted hydrazide derivatives of 7-substituted amino-3-methylene-cepham-4-carboxylic acids in high yields from inexpensive penicillin derivatives.

Other objects and advantages of the present invention will become apparent from the following description.

The present invention provides a compound of the formula

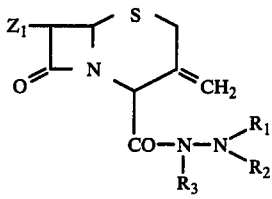
(I)

wherein $R_1$ represents an alkyl group containing at least 3 carbon atoms, a cycloalkyl group, or a substituted or unsubstituted aryl group; one of $R_2$ and $R_3$ represents a hydrogen atom, and the other a hydrogen atom, an alkyl group containing at least 3 carbon atoms, a cycloalkyl group or a substituted or unsubstituted aryl group; or $R_1$ and $R_2$ together form a heterocyclic ring directly or through a hetero atom together with the nitrogen atom to which they are attached, and $R_3$ represents a hydrogen atom; and $Z_1$ represents an amino group or an amino group protected by an amino-protecting group, and its acid addition salt.

In formula (I), the alkyl group may be a straight chain or branched chain, and contains at least 3 carbon atoms, preferably 3 to 8, more preferably 3 to 7, carbon atoms. Examples of such alkyl group include n- or iso-propyl, n-, iso-, sec- or tert-butyl, n-, iso-, sec-, tert- or neo-pentyl, n-, iso-, sec- or tert-hexyl, n-, iso-, sec-, or tert-heptyl, and n-, iso-, sec-, or tert-octyl group. Of these, the n- or iso-propyl, n-, iso- or tert-butyl, n-, iso-, sec- or neopentyl, and n-, iso- or sec-hexyl are especially preferred.

The cycloalkyl group contains at least 3, preferably 5 to 8, more preferably 5 to 7, carbon atoms, and includes, for example, cyclopropyl, cyclobutyl, cyclopentyl, cyclohexyl, cycloheptyl, cyclooctyl, and methyl cyclohexyl. Of these, the cyclopentyl and cyclohexyl are especially suitable.

The aryl group may be mono- or poly-nuclear, and includes, for example, phenyl and naphthyl. The phenyl is especially preferred. The aryl group may be unsubstituted, or substituted. When it is substituted, suitable substituents are, for example, lower alkyl groups containing 1 to 4 carbon atoms, preferably 1 or 2 carbon atoms, such as methyl or ethyl; lower alkoxy groups containing 1 to 4 carbon atoms, preferably 1 or 2 carbon atoms, such as methoxy or ethoxy; halogen atoms such as chlorine, bromine iodine or fluorine; lower haloalkyl groups such as trifluoromethyl; lower alkoxycarbonyl groups such as methoxycarbonyl or ethoxycarbonyl; lower alkanoyloxy groups such as acetyloxy or propionyloxy; a cyano group; and a nitro group. Of these, the lower alkyl and lower alkoxy groups are suitable. At most 3, preferably 1 or 2, such substituents can be present on the aryl group.

In formula (I), $R_1$ and $R_2$ can form a heterocyclic ring either directly or through a hetero atom together with the nitrogen atom to which they are bonded. Examples of the hetero atom are oxygen, sulfur and nitrogen atoms. The number of hetero atoms is suitably one. The heterocyclic ring may contain at least 3 members, conveniently 5 or 6 members, especially 6 members, and may be substituted by at least one, preferably only one, of the substituents described above with regard to the substituted aryl. Thus, examples of the heterocyclic ring include aziridine pyrrolidine, piperidine, imidazoline, 1,4-piperazine, oxazolidine, 1,4-morpholine, 1,4-thiomorpholine, 1,2,3,4-tetrahydroquinoline, and 1,2,3,4-tetrahydroisoquinoline. Of these, the pyrrolidine, piperidine, 1,4-morpholine, 1,4-piperazine, and 1,4-thiomorpholine are especially preferred.

The group $Z_1$ present at the 7-position of the cepham ring is an amino group ($-NH_2$), or an amino group protected by an amino-protecting group. Any amino-protecting groups can be used which can be removed without cleaving the $\beta$-lactam moiety of the cepham ring. The amino group protected by an amino-protecting group can be expressed by the following formula

wherein one of $R_5$ and $R_6$ is a monovalent amino-protecting group and the other a hydrogen atom; of $R_5$ and $R_6$ together form a divalent amino-protecting group. Typical examples of the monovalent amino-protecting group include (a) organic monocarbonyl groups of the formula $$R_7CO- \qquad (IV)$$

(b) organic silyl groups, and (c) a triphenylmethyl group.

In formula (IV), $R_7$ represents a hydrogen atom, a lower alkyl group, a lower alkenyl group, a lower alkoxy group, a lower alkylthio group, a cycloalkyl group containing 3 to 8 carbon atoms, a cycloalkenyl group containing 3 to 8 carbon atoms, an aryl group containing 6 to 10 carbon atoms, an aralkyl group containing 7 to 12 carbon atoms, an aryloxy group containing 6 to 10 carbon atoms, an aralkoxy group containing 7 to 12 carbon atoms, or a 5- or 6-membered heterocyclic ring containing at least one oxygen, nitrogen or sulfur atom. Each of the above groups may be substituted by a lower alkoxy group, a lower alkylthio group, a cycloalkyloxy group containing 3 to 8 carbon atoms, a cycloalkenyloxy group containing 3 to 8 carbon atoms, a cycloalkylthio group containing 3 to 8 carbon atoms, a cycloalkenylthio group containing 3 to 8 carbon atoms, an aryloxy group containing 6 to 10 carbon atoms, an aralkoxy group containing 7 to 12 atoms, a nitro group, a cyano group, an amino group, a hydroxyl group, a mercapto group, or a halogen atom. When a free amino group, hydroxyl group, or mercapto group is present in the organic monocarbonyl group, such a group may be protected by a protecting group. Such an instance is also within the scope of the present invention. All groups that are usually employed as protecting groups for an amino group can be used to protect such a free amino group. Examples include trichloroethoxycarbonyl, benzyloxycarbonyl, p-nitrobenzyloxycarbonyl, p-toluenesulfonyl, formyl, tertiary butoxycarbonyl, p-methoxybenzyloxycarbonyl, trityl, 2-nitrophenylthio, 2,4-dinitrophenylthio, and phthaloyl, which are generally easily removed. Protecting groups for the hydroxyl or mercapto group include all protecting groups usually employed for a hydroxyl group. For example, they include benzyloxycarbonyl, 4-nitrobenzyloxycarbonyl, 4-methoxylbenzylcarbonyl, tertiary butoxycarbonyl, 2,2,2-tri-chloroethoxycarbonyl, trifluoroacetyl, benzyl, trityl, and methoxymethyl which can be easily removed.

The term "lower", as used in this invention, means that groups modified by this word contain up to 5 carbon atoms.

Thus, typical examples of the organic monocarbonyl groups of formula (IV) include formyl, acetyl, propionyl, butyryl, pivaloyl, acryloyl, cyclohexylcarbonyl, cyclopentylacetyl, dihydrophenylacetyl, methoxyacetyl, methylthioacetyl, cyclohexylthioacetyl, cyclohexyloxyacetyl, dihydrophenoxyacetyl, dihydrophenylthioacetyl, benzoyl, tolyl, naphthoyl, α-methylnaphthoyl, phenylacetyl, phenylpropionyl, phenylbutyryl, naphthylacetyl, phenoxyacetyl, benzyloxycarbonyl, naphthoxycarbonyl, phenoxycarbonyl, 2-phenoxypropionyl, 1H (or 2H)-tetrazolylacetyl, thienylacetyl, thienylpropionyl, furylacetyl, piperazinylacetyl, pyrrolidinylacetyl, pyrrolidinylpropionyl, benzothiazolylacetyl, oxazolylacetyl, benzoxazolylacetyl, thiazolylacetyl, pyrazolylacetyl, indolylacetyl, quinolylacetyl, triazolylacetyl, thiadiazolylacetyl, 2-pyridylcarbonyl, methoxycarbonyl, and 2-furyloxycarbonyl.

Typical examples of the organic silyl group are trimethylsilyl, triethylsilyl, tri-n-propylsilyl, tri-isopropylsilyl, tri-n-butylsilyl, tri-iso-butylsilyl, and tri-sec-butylsilyl.

Of these monovalent amino-protecting groups, the organic monocarbonyl groups, particularly those of formula (IV) in which $R_7$ represents a lower alkyl group, a lower alkoxy group, a cycloalkyl group containing 3 to 8 carbon atoms, an aralkyl group containing 7 to 12 carbon atoms, an aralkoxy group containing 7 to 12 carbon atoms, a 5- or 6-membered heterocyclic group containing at least one oxygen, nitrogen or sulfur atom, or a $C_{6-10}$ aryloxy-lower alkyl group, are especially preferred. Specific preferred examples are acetyl, methoxycarbonyl, tertbutyloxycarbonyl, cyclohexylacetyl, phenylacetyl, benzyloxycarbonyl, 2-thienylacetyl, and phenoxyacetyl.

On the other hand, typical examples of the divalent amino-protecting groups include (d) organic dicarbonyl groups of the formula

wherein $R_8$ represents a lower alkylene group, a lower alkenylene group, or a substituted or unsubstituted arylene group, preferably containing 6 to 12 carbon atoms, and (e) groups of the formula

wherein $R_9$ represents a hydrogen atom, a lower alkyl group, an aralkyl group, or an aryl group, and $R_{10}$ represents a lower alkyl group, an aralkyl group, or an aryl group. Typical examples of the organic dicarbonyl groups of formula (V) include succinoyl, maleoyl, substituted or unsubstituted phthaloyl, naphthalene-1,2-dicarbonyl, naphthalene-2,3-dicarbonyl, and naphthalene-1,8-dicarbonyl.

Specific examples of the group of formula (VI) are isopropylidene, cyclopentylidene, cyclohexylidene, benzylidene, p-methoxybenzylidene, and p-nitrobenzylidene.

Of these divalent amino-protecting groups, the organic dicarbonyl groups, especially substituted or unsubstituted phthaloyl, particularly the latter, are preferred. The substituent on the benzene ring in the substituted phthaloyl is not particularly limited, but may be any desired inert substituent. At least one of such substituents can be present at any desired substitutable position on the benzene ring. Where two or more substituents are present, they may be different from each other. Or they may be linked to each other to form a ring. The inert substituents are, for example, lower alkyl groups, lower alkoxy groups, lower alkylthio groups, methylenedioxy groups, and halogen atoms. Examples of preferred phthaloyl groups containing such substituents include 3,6-dimethylphthaloyl, 4,5-dimethylphthaloyl, 3-methoxyphthaloyl, 4-methoxyphthaloyl, 3,4-dimethoxyphthaloyl, 4,5-dimethoxyphthaloyl, 3-methylthiophthaloyl, 3,4-methylenedioxyphthaloyl, 4,5-methylenedioxyphthaloyl, 3-chlorophthaloyl, 4-chlorophthaloyl, 4-bromophthaloyl, 4,5-dichlorophthaloyl, 3,4,5,6-tetrachlorophthaloyl, and 3,4,5,6-tetrabromophthaloyl.

Especially preferred species of the group $Z_1$ in formula (I) above are amino, phenylacetamido, phenoxyacetamido, and phthalimido groups.

Preferred compounds of formula (I) are those in which $R_1$ represents an alkyl group containing 3 to 8 carbon atoms, a cycloalkyl group containing 5 to 8 carbon atoms, or a substituted or unsubstituted phenyl group; and one of $R_2$ and $R_3$ represents a hydrogen atom, and the other a hydrogen atom, an alkyl group containing 3 to 8 carbon atoms, a cycloalkyl group containing 5 to 8 carbon atoms, or a substituted or unsubstituted phenyl group.

Another preferred group of compounds of formula (I) includes those in which $R_1$ and $R_2$ form a heterocyclic ring together with the nitrogen atom to which they are bonded, either directly or through one hetero atom selected from the group consisting of nitrogen, oxygen, and sulfur atoms and $R_3$ represents a hydrogen atom.

Especially preferred compounds within the definition of formula (I) are expressed by the following formula

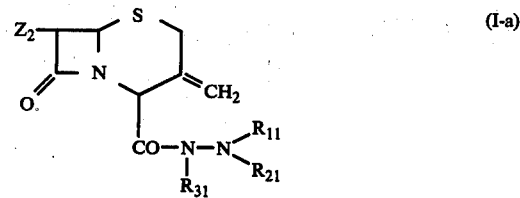

wherein $R_{11}$, $R_{21}$ and $R_{31}$, independently from each other, represent a hydrogen atom, an alkyl group containing 3 to 6 carbon atoms, a cycloalkyl group containing 5 to 7 carbon atoms, or a phenyl group optionally substituted by an alkyl or alkoxy group containing 1 to 4 carbon atoms; or $R_{11}$ and $R_{21}$ together form a 5- or 6-membered heterocyclic ring together with the nitrogen atom to which they are attached, either directly or through one hetero atom selected from the group consisting of nitrogen, oxygen and sulfur, with the proviso that $R_{11}$ represents the groups defined above other than hydrogen, and at least one of $R_{21}$ and $R_{31}$ represents a hydrogen atom; and $Z_2$ represents a phenylacetamido phenoxyacetamido, or phthalimido group.

Especially preferred compounds of formula (I-a) are those in which $R_{11}$ and $R_{31}$, independently from each other, represent an alkyl containing 3 to 6 carbon atoms, a cycloalkyl group containing 5 to 7 carbon atoms, or a phenyl group substituted by an alkyl or alkoxy group containing 1 to 4 carbon atoms, and $R_{21}$ is a hydrogen atom.

Typical examples of the compounds of formula (I) or (I-a) are listed below.

(1) 7β-phenoxyacetamido-3-methylene-cepham-4-carbo-N,N'-diisopropyl hydrazide,
(2) 7β-phenylacetamido-3-methylene-cepham-4-carbo-N,N'-diisopropyl hydrazide,
(3) 7β-acetamido-3-methylene-cepham-4-carbo-N,N'-diisopropyl hydrazide,
(4) 7β-2'-thienylacetamido-3-methylene-cepham-4-carbo-N,N'-diisopropyl hydrazide,
(5) 7β-cyclohexylacetamido-3-methylene-cepham-4-carbo-N,N'-diisopropyl hydrazide,
(6) 7β-phenoxyacetamido-3-methylene-cepham-4-carbo-N,N'-di-n-propyl hydrazide,
(7) 7β-phenylacetamido-3-methylene-cepham-4-carbo-N,N'-di-n-propyl hydrazide,
(8) 7β-cyclohexylacetamido-3-methylene-cepham-4-carbo-N,N'-di-n-propyl hydrazide,
(9) 7β-2'-thienylacetamido-3-methylene-cepham-4-carbo-N,N'-di-n-propyl hydrazide
(10) 7β-acetamido-3-methylene-cepham-4-carbo-N,N'-di-n-propyl hydrazide,
(11) 7β-phenoxy-acetamido-3-methylene-cepham-4-carbo-N,N'-dicyclohexyl hydrazide,
(12) 7β-phenylacetamido-3-methylene-cepham-4-carbo-N,N'-dicyclohexyl hydrazide,
(13) 7β-2'-thienylacetamido-3-methylene -cepham-4-carbo-N,N'-dicyclohexyl hydrazide,
(14) 7β-acetamido-3-methylene-cepham-4-carbo-N,N'-dicyclohexyl hydrazide,
(15) 7β-cyclohexylacetamido-3-methylene-cepham-4-carbo-N,N'-dicyclohexyl hydrazide,
(16) 7β-phenoxyacetamido-3-methylene-cepham-4-carbo-N'-p-methoxyphenyl hydrazide,
(17) 7β-phenylacetamido-3-methylene-cepham-4-carbo-N'-p-methoxyphenyl hydrazide,
(18) 7β-acetamido-3-methylene-cepham-4carbo-N'-p-methoxyphenyl hydrazide,
(19) 7β-cyclohexylacetamido-3-methylene-cepham-4-carbo-N'-p-methoxyphenyl hydrazide,
(20) 7β-2'-thienylacetamido-3-methylene-cepham-4-carbo-N'-p-methoxyphenyl hydrazide,
(21) 7β-phenoxyacetamido-3-methylene-cepham-4-carbo-N',N'-1',4'-tetramethylene hydrazide,
(22) 7β-phenylacetamido-3-methylene-cepham-4-carbo-N',N'-1',4'-tetramethylene hydrazide,
(23) 7β-acetamido-3-methylene-cepham-4-carbo-N',N'-1',4'-tetramethylene hydrazide,
(24) 7β-2'-thienylacetamido-3-methylene-cepham-4-carbo-N',N'-1',4'-tetramethylene hydrazide,
(25) 7β-cyclohexylacetamido-3-methylene-cephem-4-carbo-N',N'-1',4'-tetramethylene hydrazide,
(26) 7β-phenoxyacetamido-3-methylene-cepham-4-carbo-N',N'-3'-oxy-1',5'-tetramethylene hydrazide,
(27) 7β-phenylacetamido-3-methylene-cepham-4-carbo-N',N'-3'-oxy-1',5'-tetramethylene hydrazide,
(28) 7β-acetamido-3-methylene-cepham-4-carbo-N',N'-3'-oxy-1',5'-tetramethylene hydrazide,
(29) 7β-cyclohexylacetamido-3-methylene-cepham-4-carbo-N',N'-3'-oxy-1',5'-tetramethylene hydrazide,
(30) 7β-2'-thienyl-acetamido-3-methylene-cepham-4-carbo-N',N'-3'-oxy-1',5'-tetramethylene hydrazide,
(31) 7β-phthalimido-3-methylene-cepham-4-carbo-N,N'-diisopropyl hydrazide,
(32) 7β-phthalimido-3-methylene-cepham-4-carbo-N,N'-di-n-propyl hydrazide,
(33) 7β-phthalamido-3-methylene-cepham-4-carbo-N'-p-methoxyphenyl hydrazide,
(34) 7β-phthalimido-3-methylene-cepham-4-carbo-N',N'-1',4'-tetramethylene hydrazide,
(35) 7β-phthalimido-3-methylene-cepham-4-carbo-N',N'-3'-oxy-1',5'-tetramethylene hydrazide,
(36) 7β-amino-3-methylene-cepham-4-carbo-N,N'-diisopropyl hydrazide,
(37) 7β-amino-3-methylene-cepham-4-carbo-N,N'-di-n-hexyl hydrazide,
(38) 7β-phenoxyacetamido-3-methylene-cepham-4-carbo-N'-p-tolyl hydrazide,
(39) 7β-3'-thienylacetamido-3-methylene-cepham-4-carbo-N'-phenyl hydrazide,
(40) 7β-acetamido-3-methylene-cepham-4-carbo-N',N'-3'-thio-1',5'-tetramethylene hydrazide,
(41) 7β-acetamido-3-methylene-cepham-4-carbo-N',N'-3'-aza-1',5'-tetramethylene hydrazide,
(42) 7β-benzyloxycarbonylamino-3-methylene-cepham-4-carbo-N,N'-di-n-propyl hydrazide, and
(43) 7β-amino-3-methylene-cepham-4-carbo-N,N'-diisopropyl hydrazide, p-toluenesulfonate salt at the amino group.

The compounds of formula (I) can be present in the form of an acid addition salt. Acids which form acid addition salts together with the compounds of formula (I) are, for example, mineral acids such as hydrochloric acid or sulfuric acid, and organic sulfonic acids such as p-toluenesulfonic acid, and benzenesulfonic acid.

According to the present invention, the compounds of formula (I) can be prepared, for example, by thermally rearranging compounds of the general formula

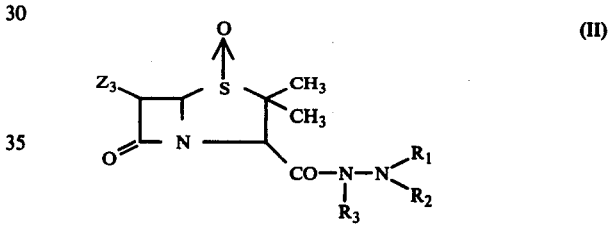

wherein $Z_3$ represents an amino group protected by an amino-protecting group, and $R_1$, $R_2$ and $R_3$ are the same as defined hereinabove, in the presence of a rearrangement promotor selected from the group of organic sulfonic acids, mono- and di-esters of phosphoric acid, organic phosphonic acids and mono-esters thereof, and diesters of phosphoryl cyanides and phosphoryl azides, if desired, subjecting the reaction product to elimination of the amino-protecting group, and if further desired, converting the reaction product to an acid addition salt.

The prominent feature of the above process of this invention is that substituted hydrazide derivatives of 6β-substituted amino-1-oxide-2,2-dimethyl-penam-3-carboxylic acids of formula (II), which can be easily derived from readily available and inexpensive penicillin derivatives, are used as starting materials.

The amino group ($Z_3$) protected by an amino-protecting group in formula (II) is the same as defined with regard to group $Z_1$ in formula (II), and $R_1$, $R_2$ and $R_3$ also have the same meanings as defined hereinabove. Thus, typical examples of the compounds of formula (II) used as starting materials in the process of this invention are as follows:

(1) 6β-phenoxyacetamido-1-oxide-2,2-dimethyl-penam-3-carbo-N,N'-diisopropyl hydrazide,
(2) 6β-phenylacetamido-1-oxide-2,2-dimethyl-penam-3-carbo-N,N'-diisopropyl hydrazide,
(3) 6β-phthalimido-1-oxide-2,2-dimethyl-penam-3-carbo-N,N'-diisopropyl hydrazide, (4) 6β-phenoxyacetamido-1-oxide-2,2-dimethyl-penam-3-carbo-N,N'-di-n-propyl hydrazide,
(5) 6β-phenylacetamido-1-oxide-2,2-dimethyl-penam-3-carbo-N,N'-di-n-propyl hydrazide,
(6) 6β-phthalimido-1-oxide-2,2-dimethyl-penam-3-carbo-N,N'-di-n-propyl hydrazide,
(7) 6β-phenoxyacetamido-1-oxide-2,2-dimethyl-penam-3-carbo-N,N'-dicyclohexyl hydrazide,
(8) 6β-phenylacetamido-1-oxide-2,2-dimethyl-penam-3-carbo-N,N'-dicyclohexyl hydrazide,
(9) 6β-phenoxyacetamido-1-oxide-2,2-dimethyl-penam-3-carbo-N'-p-methoxyphenyl hydrazide,
(10) 6β-phenylacetamido-1-oxide-2,2-dimethyl-penam-3-carbo-N'-p-methoxyphenyl hydrazide,
(11) 6β-phenoxyacetamido-1-oxide-2,2-dimethyl-penam-3-carbo-N',N'-1',4'-tetramethylene hydrazide,
(12) 6β-phenylacetamido-1-oxide-2,2-dimethyl-penam-3-carbo-N',N'-1',4'-tetramethylene hydrazide,
(13) 6β-phenoxyacetamido-1-oxide-2,2-dimethyl-penam-3-carbo-N',N'-3'-oxy-1',5'-tetramethylene hydrazide,
(14) 6β-phenylacetamido-1-oxide-2,2-dimethyl-penam-3-carbo-N',N'-3'-oxy-1',5'-tetramethylene hydrazide,
(15) 6β-phthalimido-1-oxide-2,2-dimethyl-penam-3-carbo-N'-p-methoxyphenyl hydrazide,
(16) 6β-phthalimido-1-oxide-2,2-dimethyl-penam-3-carbo-N',N'-1',4'-tetramethylene hydrazide,
(17) 6β-thienylacetamido-1-oxide-2,2-dimethyl-penam-3-carbo-N,N'-diisopropyl hydrazide,
(18) 6β-2'-thienylacetamido-1-oxide-2,2-dimethyl-penam-3-carbo-N',N'-1',4'-tetramethylene hydrazide, and
(19) 6β-2'-thienylacetamido-1-oxide-2,2'-dimethyl-penam-3-carbo-N',N'-3'-oxy-1',5'-tetramethylene hydrazide.

Another feature of the process of this invention is that the thermal rearrangement of the compound of formula (II) is carried out in the presence of a rearrangement promotor selected from the group consisting of organic sulfonic acids, mono- and di-esters of phosphoric acid, organic phosphonic acids, monoesters thereof, and diesters of phosphoryl cyanides and phosphoryl azides.

As stated above, D. H. R. Barton et. al. reported that thermal rearrangement of a substituted hydrazine derivative of a certain penicillin-1-oxide in the presence of pyridine and ortho-phosphoric acid afforded the corresponding desacetoxycephalosporanic acid derivatives. The present inventors, on the other hand, found that thermal rearrangement of the compound of formula (II) in the presence of the specific rearrangement promotor gives a novel thermally rearranged product of formula (I) whose formation is not appreciable when pyridine and ortho-phosphoric acid are used.

The rearrangement promotors that can be advantageously used in the thermal rearrangement in accordance with the present invention are described in detail below.

(a) Organic sulfonic acids

The organic sulfonic acids that can be used in this invention are compounds containing at least one sulfonic acid group (—SO$_3$H) in the molecule, which are expressed by the following formula $$R_{12}(SO_3H)_n \qquad (VII)$$

wherein R$_{12}$ represents a hydrocarbon residue having a valence of n, which may contain hetero atoms, and n is an integer of at least 1, preferably 1 to 3, especially 1.

The hetero atoms that can be optionally contained in the hydrocarbon residue R$_{12}$ include, for example, nitrogen, oxygen, sulfur and halogen atoms. Where two or more hetero atoms are present, they may be different from each other. The hydrocarbon residue may be saturated or unsaturated, and may be any of aliphatic, alicyclic, aromatic, araliphatic, and heterocyclic groups. Generally, the hydrocarbon residue may contain 1 to 15, preferably 1 to 12, carbon atoms. Suitable examples of the group R$_{12}$ are lower alkyl groups, cycloalkyl groups containing 3 to 12 carbon atoms, aryl groups containing 6 to 14 carbon atoms, aralkyl groups containing 7 to 15 carbon atoms, and 5- or 6-membered heterocyclic rings. Each of these groups may be substituted by a halogen atom, a lower alkyloxy group, an acyl group, a lower alkyloxy carbonyl group, a lower alkyl group, a nitro group, or a cyano group, etc.

Typical examples of the organic sulfonic acids of formula (VII) are methanesulfonic acid, ethanesulfonic acid, n-propanesulfonic acid, trifluoromethanesulfonic acid, aminoethanesulfonic acid, 1-octanesulfonic acid, benzenesulfonic acid, p-toluenesulfonic acid, p-methoxybenzenesulfonic acid, 2-mesitylsulfonic acid, p-acetylbenzenesulfonic acid, aniline-2-sulfonic acid, naphthalene-1-sulfonic acid, naphthalene-1,5-disulfonic acid, naphthalene-2,6-disulfonic acid, anthraquinone-2,6-disulfonic acid, benzylsulfonic acid, d-10-camphorsulfonic acid, pyridine-2-sulfonic acid, 3- or 4-pyridineethanesulfonic acid, and picolinesulfonic acid. Of these, the methanesulfonic acid, d-10-camphorsulfonic acid and p-toluenesulfonic acid are especially preferred.

(b) Mono- or di-esters of phosphoric acid
Suitable esters are those of the formula

(VIII)

wherein R$_{13}$ represents a monovalent hydrocarbon residue optionally containing hetero atoms, and R$_{14}$ represents a hydrogen atom, or a monovalent hydrocarbon residue optionally containing hetero atoms.

Examples of the hetero atoms optionally contained in the monovalent hydrocarbon group in formula (VIII) are nitrogen, oxygen, sulfur, and halogen atoms. These hetero atoms may be present in the side chains or as a member of the ring. When there are two or more hetero atoms, they may be different from each other. The hydrocarbon group may be saturated or unsaturated, and may be any of aliphatic alicyclic, aromatic, and araliphatic groups. It may contain generally 1 to 12, preferably 1 to 10, carbon atoms. Examples of suitable monovalent hydrocarbon residues include lower alkyl groups, cycloalkyl groups containing 3 to 8 carbon atoms, aryl groups containing 6 to 10 carbon atoms, aralkyl groups containing 7 to 12 carbon atoms, and 5- or 6-membered heterocyclic groups. Each of these groups may be substituted by a halogen atom, a lower alkoxy group, a nitro group, a cyano group, an acyl group, and a lower alkyl group. Of these, the lower alkyl groups, cyclohexyl group, phenyl group, naphthyl group and benzyl group are especially preferred.

Specific examples of the mono- or di-esters of phosphoric acid of formula (VIII) are diethyl phosphate, di-n-propyl phosphate, dibenzyl phosphate, diphenyl phosphate, n-propyl benzyl phosphate, isopropyl benzyl phosphate, di-n-butyl phosphate, di-diphenyl phosphate, bis-(o-chlorophenyl) phosphate, di-α-naphthyl phosphate, bis-(p-methoxyphenyl) phosphate, methyl dihydrogen phosphate, ethyl dihydrogen phosphate, n-butyl dihydrogen phosphate, p-chlorophenyl dihydrogen phosphate, cyclohexyl dihydrogen phosphate, phenyl dihydrogen phosphate, p-methyl dihydrogen phosphate, benzyl dihydrogen phosphate, and β-naphthyl dihydrogen phosphate.

(c) Organic phosphonic acids or monoester thereof

Suitable compounds are those expressed by the following formula

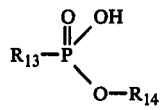

(IX)

wherein $R_{13}$ and $R_{14}$ are the same as defined above.

Specific examples of these compounds are ethyl phosphonic acid, n-propyl phosphonic acid, isopropyl phosphonic acid, n-butyl phosphonic acid, cyclohexyl phosphonic acid, phenyl phosphonic acid, benzyl phosphonic acid, methyl hydrogen methylphosphonate, ethyl hydrogen methylphosphonate, and ethyl hydrogen phenylphosphonate.

(d) Diesters of phosphoryl cyanides or azides

These diesters can be expressed by the formula

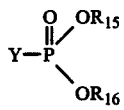

(X)

wherein $R_{15}$ and $R_{16}$, independently from each other, represent a monovalent hydrocarbon group, and Y is —CN or —N$_3$.

The monovalent hydrocarbon group in formula (X) includes, for example, lower alkyl groups, aryl groups containing 6 to 10 carbon atoms, and aralkyl groups containing 7 to 12 carbon atoms.

Typical examples of the compounds of formula (X) are diethyl phosphoryl cyanide, di-isopropyl phosphoryl cyanide, di-n-butyl phosphoryl cyanide, diphenyl phosphoryl cyanide, diethyl phosphryl azide, di-isopropyl phosphoryl azide, di-n-butyl phosphoryl azide, and diphenyl phosphoryl azide. Of these, diethyl phosphoryl cyanide and diphenyl phosphoryl azide are especially preferred.

Among the rearrangement promotors cited above, the organic sulfonic acids are especially preferred.

The amount of the rearrangement promotor is not critical, but can be varied over a wide range according, for example, to the type of the rearrangement promotor, the type of the starting compound of formula (II), and the reaction conditions. Generally, it is used in an amount of at least 0.01 mole per mole of the compound of formula (II). There is no particular upper limit to the amount of the promotor, but too great an amount does not bring about any corresponding technical advantage, and is uneconomical. Hence, sufficient amounts are not more than 10 moles per mole of the compound of formula (II), and the preferred amount is 0.05 to 5 moles. When the promotor is the organic sulfonic acid, the mono- or di-esters of phosphoric acid, and the organic phosphonic acids or their monoesters, the amount is desirably 0.05 to 1.5 moles, especially 0.1 to 1.0 mole, per mole of the compound of formula (II). On the other hand, the amount of the diester of phosphoryl cyanide or phosphoryl azide is desirably 0.8 to 5 moles, preferably 1 to 3 moles, per mole of the compound of formula (II).

The thermal rearrangement can be preformed in the absence of a solvent, but is generally carried out in an inert organic solvent. Examples of usable solvents include hydrocarbons such as benzene, toluene, xylene, tetralin, heptane, octane, and nonane; halogenated hydrocarbons such as chloroform, carbon tetrachloride, dichloroethane, trichloroethane, chlorobenzene, and bromobenzene; ethers such as tetrahydrofuran, dioxane, anisole and diglyme; and aprotic polar organic solvents such as acetonitrile, propionitrile, N,N-dimethylformamide, N,N-dimethylacetamide, dimethyl sulfoxide, tetramethylene sulfone, and hexamethylphosphoramide. They can be used either alone or in admixture of two or more. Of these, the aprotic polar organic solvents are especially suitable.

The reaction temperature is not critical, and can be varied over a wide range according, for example, to the types of the rearrangement promotor and/or the compound of formula (II), and the reaction conditions. Generally, the reaction is carried out at an elevated temperature of at least 50° C. The upper limit of the temperature is not strict, but since undesirable side reactions or decomposition reactions increase at very high temperatures, it is generally advantageous to employ temperatures of not more than 200° C. Preferred temperatures are 60 to 170° C., particularly 70 to 150° C.

The reaction can generally be completed in 1 to 24 hours under the above conditions.

According to the present invention, it has been found that the thermal rearrangement reaction is further promoted by the presence of a tertiary nitrogen-containing cyclic compound in addition to the rearrangement promotor.

Useful tertiary nitrogen-containing cyclic compounds are those containing at least one, particularly 1 to 2, tertiary nitrogen atoms as ring members, and include, for example, pyridine, 2-ethyl pyridine, 3-ethyl pyridine, 4-ethyl pyridine, 5-ethyl-2-methyl pyridine, 2-methoxy pyridine, 4-methoxy pyridine, 3-methoxy pyridine, 2-chloropyridine, 4-chloropyridine, 2-methyl-3-chloropyridine, 3-nitropyridine, 4-nitropyridine, α-picoline, β-picoline, γ-picoline, 2,3-lutidine, 2,6-lutidine, phyrimidine, and quinoline. Of these, tertiary nitrogen-containing heteroaromatic compounds such as pyridine and substituted pyridines are preferred.

The amount of the tertiary nitrogen-containing cyclic compound is not critical, but can be varied over a wide range according to the type of the rearrangement promotor and other reaction conditions. Generally, the amount is advantageously at least 0.1 mole, preferably 0.5 to 2 moles, more preferably 0.7 to 1.8 moles, per mole of the rearrangement promotor.

The tertiary nitrogen-containing cyclic compound can be present in free form in the reaction system, or may partially or wholly form a salt with the rearrangement promotor. Furthermore, the tertiary nitrogen-containing cyclic compound can be added to the reaction system in the form of its salt with the rearrangement promotor.

According to the rearrangement reaction of this invention, water is formed as a by-product as the reaction proceeds. The by-product water does not markedly impede the progress of the rearrangement reaction, but is desirably removed from the reaction system during the reaction. This can be accomplished, for example, by adding a dehydrating substance such as molecular sieves or anhydrous sodium sulfate to the reaction system, or by incorporating a solvent forming an azeotrope with water, for example, benzene, toluene or dioxane in the reaction system and removing water azetropically while evaporating it off.

Thus, a compound of formula

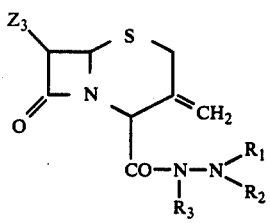
(I-b)

wherein $R_1$, $R_2$, $R_3$ and $Z_3$ are the same as defined hereinabove, can be obtained usually in the form of a mixture with a compound of the formula

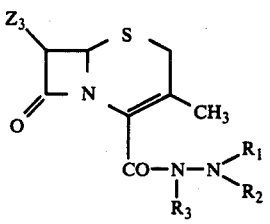

wherein $R_1$, $R_2$, $R_3$ and $Z_3$ are the same as defined hereinabove.

According to the present invention, the compound of formula (I-b) can be converted to a compound of the formula

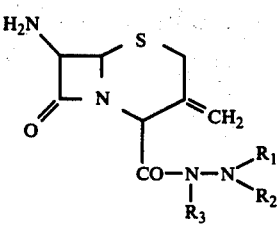
(I-c)

wherein $R_1$, $R_2$ and $R_3$ are the same as defined hereinabove, by subjecting it to a reaction of eliminating the amino-protecting group.

The reaction of eliminating the amino-protecting group is known per se, and includes, for example, hydrolysis, decomposition with phosphorus pentachloride and a lower alcohol, and decomposition with hydrazine. These methods can be chosen properly according to the type of the amino-protecting group to be removed, and the choice is known to those skilled in the art.

For example, when the amino-protecting group to be removed is the organic monocarbonyl group cited hereinabove, it can be split off by hydrolysis, or by treating it with phosphorus pentachloride and a lower alcohol. When the amino-protecting group is the organic dicarbonyl group, especially a substituted or unsubstituted 1,2-phthaloyl group, the hydrazine decomposition is an effective means of eliminating it.

The hydrolysis can be performed by treating the compound of formula (I-b) in which the amino-protecting group is an organic monocarbonyl group with an aqueous strong orgaic acid such as trifluoroacetic acid or p-toluenesulfonic acid, or an aqueous alkali such as an aqueous solution of sodium hydroxide, an aqueous solution of potassium hydroxide, an aqueous solution of sodium bicarbonate, an aqueous solution of sodium carbonate, or an aqueous solution of pyridine at a temperature up to the boiling point of the reaction mixture in an inert organic solvent of the types exemplified hereinabove.

The deprotection with phosphorus pentachloride and a lower alcohol is performed by treating the compound of formula (I-b) in which the amino-protecting group is an organic monocarbonyl group with phosphorus pentachloride/pyridine complex (1:1) at a temperature of about 10° C. or less in an inert organic solvent of the types exemplified hereinabove, then adding a lower alcohol such as methanol, and treating the mixture with a great quantity of water.

The hydrazine decomposition, especially effective for the compound of formula (I-b) in which the amino-protecting group is an organic dicarbonyl group, is performed by treating the compound with hydrazine or its hydrate in the absence of solvent or in an inert organic solvent of the types exemplified hereinabove at a temperature up to the boiling point of the reaction mixture.

The 3-methylenecephalosporanic acid derivative of formula (I) prepared by the rearrangement reaction in accordance with the process of this invention can be isolated from the reaction mixture and purified by various methods known per se, such as extraction, recrystallization, column chromatography, or thin-layer chromatography.

If desired, the resulting compound of formula (I) can be converted to an acid addition salt. The conversion to acid addition salts can be performed easily in accordance with known means by treating the compound of formula (I) with an inorganic acid such as hydrogen chloride, hydrogen bromide or sulfuric acid, or an organic sulfonic acid such as p-toluenesulfonic acid, benzenesulfonic acid, methanesulfonic acid, α-naphthalenesulfonic acid, β-naphthalenesulfonic acid, or d-10-camphorsulfonic acid.

Some of the compounds of formula (II) used as starting materials in the process of this invention are known. When they are novel, they can be prepared in the same way as in the preparation of the known species.

For example, the compound of formula (II) can be prepared easily by reacting an S-oxide of a 6-substituted aminopenicillanic acid of the formula

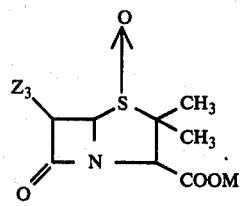
(XI)

wherein M represents a hydrogen atom or an alkali metal, preferably potassium or sodium, and $Z_3$ is the same as defined above, (obtained by oxidizing the 6-substituted aminopenicillanic acid or its alkali metal salt which is readily available industrially) with a substituted hydrazine of the formula

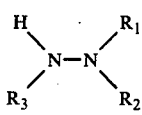
(XII)

wherein $R_1$, $R_2$ and $R_3$ are the same as defined above, in an inert medium in the presence of a condensing agent of the phosphoryl cyanide, phosphoryl azide or carbodiimide series; or by reacting a mixed acid anhydride (obtained by reacting the carboxylic acid of formula (XI) with a carboxylic acid halide such as ethyl chlorocarbonate in the presence of triethylamine) with the substituted hydrazide.

Specific examples of the condensing agent are diethyl phosphoryl cyanide, diphenyl phosphoryl azide and dicyclohexyl carbodiimide. Examples of preferred inert media used in this process are halogenated hydrocarbons such as dichloromethane, chloroform, dichloroethane or tetrachloroethylene, ethers such as dioxane or tetrahydrofuran, ketones such as methyl ethyl ketone or acetone, esters such as ethyl acetate or butyl acetate; and acetonitrile, dimethyl formamide, formamide, hexamethylphosphorylamide, dimethyl acetamide, and dimethyl sulfoxide. They can be used either alone or in admixture of two or more.

The amount of the condensing agent is preferably 1 to 1.3 moles per mole of the 6-substituted aminopenicillanic acid S-oxide of formula (XI). The reaction temperature is not more than 45° C., preferably —10° C. to 30° C. Preferably, the condensing agent is added at about 0° C. The reaction time differs according, for example, to the type of the starting compound of formula (XI), the type of the condensing agent, or other reaction conditions, but is usually 30 minutes to 30 hours.

It has been found that better results can be obtained by performing the reaction in the presence of a tertiary amine. The compound of formula (II) can be produced in higher yields by using 1 to 1.2 moles of the tertiary amine per mole of the 6-aminopenicillanic acid derivative of formula (XI).

Any tertiary amines can be used, but typical examples are triethylamine, N-methyl morpholine, triethylenediamine, pyridine, α-picoline, γ-picoline, 2,4,6-trimethyl pyridine, N,N-dimethylaniline, N,N-diethylaniline, and N,N,N',N'-tetraethylenediamine.

After the reaction, the compound of formula (II) is obtained from the reaction mixture in a usual manner. For example, it can be easily obtained by washing the reaction mixture with an aqueous acid and then an alkali solution, and then evaporating off the solvent. The resulting compound of formula (II) can be directly used in the thermal rearrangement process described above. If desired, it can be purified in a usual manner such as recrystallization.

According to the process of this invention described above, the novel substituted hydrazide derivatives of 7-(substituted)amino-3-methylene-cepham-4-carboxylic acid or the acid addition salts thereof can be easily obtained in high yields from readily available inexpensive 6-substituted aminopenicillanic acid derivatives.

Since the substituted hydrazide derivatives of 7-(substituted)amino-3-methylene-cepham-4-carboxylic acids of formula (I) provided by this invention have an active methylene group at the 3-position, they are very useful as intermediates for the synthesis of various cephalosporin-type antibiotics. For example, from the compound of formula (I-b), cephalothin and cephazolin now in use as medicines having superior antibacterial activity can be prepared more advantageously by the synthetic route shown below than by the conventional methods.

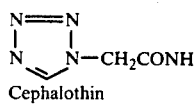

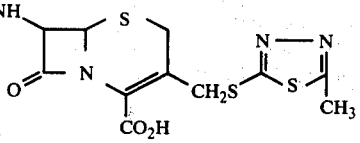

Step 1: Formation of carboxylic acid by oxidative cleavage of protecting-group.
  Reagents ... Pb(OAc)₄, pyridine, benzene, H₂O
  Reaction conditions ... below room temperature, about 10 minutes
Step 2: Oxidative acetoxylation reaction
  Reagents ... SeO₂, Ac₂O
  Reaction conditions ... above 100° C., several hours
Step 3: Elimination of amino-protecting group
  Reagents ... (1) (CH₃)₃SiCl, (C₂H₅)₃N and (2) PCl₅/pyridine; CH₃OH; H₂O
  Reaction conditions ... (1) below 10° C., several hours; (2) below 10° C., several hours
Step 4-1: Substitution of 3-acetoxy group
  Reagents ...

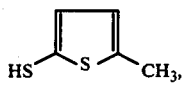

NaHCO₃, H₂O
  Reaction conditions ... about 50 to 60° C., 7 to 10 hours
Step 4-2: Same as in Step 4-1
Step 5-1: Acylation of 7-amino group
  Reagents ...

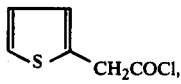

NaHCO₃, H₂O
  Reaction conditions ... below 10° C., several hours
Step 5-2: Acylation of 7-amino group
  Reagents ...

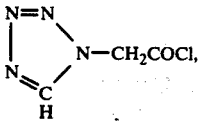

NaHCO₃, H₂O
  Reaction conditions ... below 10° C., several hours
  (Ac=CH₃CO)

Treatment of the substituted hydrazide derivatives of 7-(substituted) amino-3-methylene-cepham-4-carboxylic acid of formula (I) provided by the present invention with ozone (for example, in methylene chloride at −78° C. to −50° C. for 1 hour) affords substituted hydrazide derivatives of 7(substituted)amino-3-oxo-cepham-4-carboxylic acid. 7-(Substituted)-amino-3-methoxy-cepham-4-carboxylic acids having antibacterial activity can be formed by treating the resulting product with diazomethane (for example, using CH₂N₂ or (C₂H₅)₂O—CH₂Cl₂ at room temperature), followed by treatment with an oxidizing agent such as lead tetra-acetate (for example, at room temperature, Pb(OAc)₄-pyridine-H₂O, benzene, 10 minutes). This product is also useful as an intermediate for the synthesis of various antibiotics.

The following Examples further illustrate the present invention.

EXAMPLE 1

(1) Preparation of 6β-phenoxyacetamodo-1-oxide-2,2-dimethyl-penam-3-carbo-N,N'-diisopropyl hydrazide:

2.196 g of 6β-phenoxyacetamidopenicillanic acid-1-oxide was dissolved in 20 ml of N,N-dimethylformamide. The solution was cooled to 0° C, and with stirring, a solution of 1.082 g of diethyl phosphoryl cyanide in 4 ml of N,N-dimethylformamide was added to this solution, followed by addition of a solution of 765 mg of N,N'-diisopropyl hydrazine in 6 ml of N,N-dimethylformamide. Furthermore, a solution of 666 mg of triethylamine in 10 ml of N,N-dimethylformamide was slowly added dropwise. The mixture was stirred for 1.5 hours at 0° C., and 400 ml of ethyl acetate was added to the reaction mixture. The mixture was washed successively with a 0.25 M aqueous solution of tartaric acid, water, a saturated aqueous solution of sodium bicarbonate, and a saturated aqueous solution of sodium chloride, and then dried over anhydrous sodium sulfate. The solvent was then distilled off. The residue was recrystallized from ether to afford 1.380 g of colorless crystals having the following characteristics.

Melting point (from a mixture of methylene chloride, ethyl acetate and diethylene): 174 – 176° C.
IR spectrum, $\nu_{max}^{nujol}$(cm⁻¹): 3250, 1760, 1700, 1650.
NMR spectrum, δ ppm (CDCl₃):
1.0 – 1.4 (12H, m),
1.50 (3H, s),
1.70 (3H, s),
4.53 (2H, s),
5.13 (1H, d, J=4Hz),
5.87 (1H, s),
6.10 (1H, q, J=4, 10Hz).

From these characteristics, this product was determined to be 6β-phenoxyacetamido-1-oxide-2,2-dimethyl-penam-3-carbo-N,N'-diisopropyl hyrazide.

(2) Preparation of 7β-phenoxyacetamido-3-methylene-cepham-4-carbo-N,N'-diisopropyl hydrazide:

1.0 g of 6β-phenoxyacetamido-1-oxide-2,2-dimethyl-penam-3-carbo-N,N'-diisopropyl hydrazide was dissolved in a solution of 25 ml of N,N-dimethylacetamide and 25 ml of benzene, and 0.1 ml of methanesulfonic acid was added to this mixture. The mixture was heated for 2 hours at a bath temperature of 110° C. During the reaction, the low boiling solvent was gradually distilled off. After cooling, 50 ml of ethyl acetate was added, and the mixture was washed four times with water. The product was dried, and the solvent was distilled off to leave an oily product which was column chromatographed over silica gel with a mixture of benzene and ethyl acetate (9:1) as eluant to afford 400 mg of a product having the following characteristics.

NMR spectrum δ (ppm):
1.02 – 1.32 (6H, m),
3.06, 3.68 (2H, AB-q, J=13.5Hz),
4.48 (2H, s), 5.02 – 5.18 (2H, d),
5.58 – 5.70 (2H, m),
6.20 (1H, s),
6.78 –7.45 (6H, m).
Ir spectrum, $\nu_{max}^{KBr}$ (cm$^{-1}$): 3300, 1760, 1685, 1650.
Mass spectrum, (m/e): 446 (M$^+$).

From the above characteristics, the product was determined to be 7β-phenoxyacetamido-3-methylene-cepham-4-carbo-N,N'-diisopropyl hydrazide.

EXAMPLE 2

(1) Preparation of 6β-phenylacetamido-1-oxide-2,2-dimethyl-penam-3-carbo-N,N'-dissopropyl hydrazide:

2.142 g of sodium 6β-phenylacetamido-1-oxide-penicillanate was dissolved in 20 ml of N,N-dimethylformamide. The solution was cooled to 0° C. To the solution was added a solution of 764 mg of N,N'-diisopropyl hydrazide in 10 ml of N,N-dimethylformamide with stirring. Furthermore, a solution of 1.082 g of diethyl phosphoryl cyanide in 10 ml of N,N'-dimethylformamide was added. When the mixture was stirred at 0° C. for 1 hour, the reaction was completed. 400 ml of ethyl acetate was added, and the mixture was washed successively with water, a 0.5M aqueous solution of tartaric acid, a saturated aqueous solution of sodium bicarbonate, and a saturated aqueous solution of sodium chloride, and dried over anhydrous sodium sulfate. The solvent was distilled off to afford 1.45 g of a product having the following characteristics.

Melting point (from a mixture of ethyl acetate and diethyl ether): 164 to 166° C.
IR spectrum $\nu_{max}^{nujol}$ (cm$^{-1}$): 3250, 1775, 1650.
NMR spectrum, δ ppm (CDCl$_3$):
1.00 – 1.50 (12H, m),
1.50 (3H, s),
1.77 (3H, s),
3.63 (2H,s),
5.00 (1H, d, J=4Hz),
5.73 (1H, s),
5.93 (1H, q, J–4, 10Hz).

From the above characteristics, the product was determined to be 6β-phenylacetamido-1-oxide-2,2-dimethyl-penam-3-carbo-N,N'-diisopropyl hydrazide.

(2) Preparation of 7β-phenylacetamido-3-methylene-cepham-4-carbo-N,N'-diisopropyl hydrazide:

1.0 g of 6β-phenylacetamido-1-oxide-2,2-dimethyl-penam-3-carbo-N,N'-diisopropyl hydrazide was dissolved in a mixture of 25 ml of N,N-dimethylacetamide and 25 ml of benzene. To the resulting mixture was added 0.1 ml of methanesulfonic acid, and the mixture heated for 2 hours at a bath temperature of 110° C. After cooling, 50 ml of ethyl acetate was added, and the mixture was washed four times with water. The product was dried over anhydrous sodium sulfate, and the solvent was distilled off. The residual oily product was chromatographed on silica gel to afford 0.2 g of a product having the following characteristics.

NMR spectrum, δ (ppm):
1.08 – 1.40 (6H, m),
3.08, 3.90 (2H, AB-q, J=14Hz),
3.68 (2H, s),
5.12 – 5.20 (2H, m),
5.45 – 5.72 (2H, m),
6.20 (1H, s),
7.10 – 7.40 (6H, bs).
IR spectrum, $\nu_{max}^{KBr}$ (cm$^{-1}$): 3350, 3250, 1760, 1650.
Mass spectrum, (m/e): 430 (M$^+$).

The product was determined to be 7β-phenylacetamido-3-methylene-cepham-4-carbo-N,N'-diisopropyl hydrazide.

EXAMPLE 3

(1) Preparation of 6β-phenoxyacetamido-1-oxide-2,2-dimethyl-penam-3-carbo-N'-p-methoxyphenyl hydrazide:

5.49 g of 6β-phenoxyacetamido-penicillanic acid-1-oxide was dissolved in 60 ml of N,N-dimethylformamide, and the solution cooled to 0° C. To the solution was added a solution of 4.54 g of diethyl phosphoryl cyanide in 20 ml of N,N-dimethylformamide. Then, a solution of 2.88 g of p-methoxyphenyl hydrazine hydrochloride in 20 ml of N,N-dimethylformamide was added to the reaction mixture. Ten minutes later, a solution of 3.33 g of triethylamine in 20 ml of N,N-dimethylformamide was added, and the mixture was stirred at 0° C for 3 hours. 500 ml of ethyl acetate was added to the reaction mixture, and the mixture was washed successively with water, a 0.5 M aqueous solution of tartaric acid, a saturated aqueous solution of sodium bicarbonate, and a saturated aqueous solution of sodium chloride, followed by drying over anhydrous sodium sulfate. The solvent was distilled off at reduced pressure, and the residue was crystallized from a mixture of ethyl acetate and diethyl ether to afford 4.57 g of crystals having the following characteristics.

Melting point (from a mixture of ethanol, methylene chloride, and diethyl ether): 191.5 – 192.5° C. (dec.).
IR spectrum, $\nu_{max}^{nujol}$ (cm$^{-1}$): 3270, 3240, 1785, 1680.
NMR spectrum, δ ppm (CDCl$_2$):
1.27 (3H, s),
1.67 (3H, s),
3.77 (3H, s),
4.50 (1H, s),
4.60 (2H, s),
5.36 (1H, d, J=4Hz),
5.96 (1H, q, J=4Hz, 10Hz).

From the above characteristics, the product was determined to be 6β-phenoxyacetamido-1-oxide-2,2-dimethyl-penam-3-carbo-N'-p-methoxyphenyl hydrazide.

(2) Preparation of 7β-phenoxyacetamido-3-methylene-cepham-4-carbo-N'-p-methoxyphenyl hydrazide:

0.5 g of 6β-phenoxyacetamido-1-oxide-2,2-dimethyl-penam-3-carbo-N'-p-methoxyphenyl hydrazide was dissolved in a mixture of 10 ml of N,N'-dimethylacetamide and 10 ml of benzene, and 0.1 g of d-10-1'-camphorsulfonic acid was added to the mixture. The mixture was heated at a bath temperature of 110° C. for 3 hours. After cooling, 50 ml of ethyl acetate was added to the reaction mixture, and the mixture was washed four times with water and then dried over anhydrous sodium sulfate. The solvent was distilled off, and the residue was chromatographed on silica gel to afford 0.1 g of a product having the following characteristics.

NMR spectrum, δ (ppm):
3.18, 3.70 (2H, AB-q, J=14Hz),
3.70 (3H, s),
4.40 (2H, s),
5.15 – 5.23 (3H, bd), 5.40 (1H, d, J=4Hz),
5.80, 5.88 (1H, d-d, J=10, 4Hz),
6.14 (1H, s),
6.68 - 7.58 (10H, m).
IR spectrum, $v_{max}^{KBr}$ (cm$^{-1}$); 3350, 3250, 1760, 1680.
Mass spectrum, (m/e): 468 (M$^+$)

The product was determined to be 7β-phenoxyacetamide-3-methylene-cepham-4-carbo-N'-p-methoxyphenyl hydrazide.

EXAMPLE 4

(1) Preparation of 6β-phenoxyacetamido-1-oxide, 2,2-dimethyl-penam-3-carbo-N',N'-3'-oxo-1',5'-tetramethylene hydrazide:

1.098 g of 6β-phenoxyacetamido-penicillanic acid-1-oxide was dissolved in 10 ml of N,N-dimethylformamide. The solution was cooled to 0° C., and a solution of 541 mg of diethyl phosphoryl cyanide in 2 ml of N,N-dimethylformamide was added with stirring. Furthermore, a solution of 330 mg of N-aminomorpholine in 3 ml of N Ndimethylformamide was added. Finally a solution of 333 mg of triethylamine in 3 ml of N N-dimethylformamide was slowly added. The reaction was terminated in about 1.5 hours. To the reaction mixture was added 200 ml of ethyl acetate, and the mixture was washed successively with a 0.25 M aqueous solution of tartaric acid, water, a saturated aqueous solution of sodium bicarbonate, and a saturated aqueous solution of sodium chloride, and then dried over anhydrous sodium sulfate. The solvent was distilled off, and the residue was crystallized from diethyl ether to afford 6β-phenoxyacetamido-1-oxide-2,2-dimethyl-penam-3-carbo-N',N'-3'-oxo-1',5'-tetramethylene hydrazide having the following characteristics.

Melting point (from ethyl acetate and chloroform): 182 - 183° C.

IR spectrum, $v_{max}^{nujol}$ (cm$^{-1}$): 3200, 1770, 1670.
NMR spectrum, δ ppm (DMSO-d$_6$):
1.15 (3H, s),
1.55 (3H, s),
2.80 (4H, bs),
3.63 (4H, bs),
4.20 (1H, s),
4.65 (2H, s),
5.23 (1H, d, J=4Hz),
5.77 (1H, q, J=4, 10Hz).

(2) Preparation of 7β-phenoxyacetamido-3-methylene-cepham-4-carbo-N',N'-3'-oxo-1',5'-tetramethylene hydrazide:

1.0 g of 6β-phenoxyacetamido-1-oxide-2,2-dimethyl-penam-3-carbo-N',N'-3'-oxo-1',5'-tetramethylene hydrazide was dissolved in a mixture of 20 ml of N,N-dimethylacetamide and 20 ml of benzene, and to the mixture was added 0.2 ml of methanesulfonic acid. The mixture was heated for 2 hours at a bath temperature of 120° C. After cooling, chloroform was added, and the mixture was washed three times with water, and then dried over anhydrous sodium sulfate. The solvent was distilled off to afford a yellowish oily residue. The residue was chromatographed on silica gel to afford 7β-phenoxyacetamido-3-methylene-cepham-4-carbo-N',N'-3'-oxo-1',5'-tetramethylene hydrazide having the following characteristics.

NMR spectrum (CDCl$_3$), δ (pm):
2.78 (4H, m),
3.17, 3.95 (4H, AB-q, J=14Hz),
3.80 (4H, m),
4.60 (2H, s),
5.30 (2H, bs),
5.5 - 5.9 (3H, m),
6.60 (1H, s),
6.90 - 7.5 (6H, m)
IR spectrum, $v_{max}^{KBr}$ (cm$^{-1}$): 3380, 3250, 1765, 1690, 1665.
Mass spectrum, (m/e): 432 (M$^+$).

EXAMPLE 5

(1) Preparation of 6η-phenoxyacetamido-1-oxide-2,2-dimethyl-penam-3-carbo-N,N'-1',5'-pentamethylene hydrazide:

12.2 g of 6β-phenoxyacetamido-1-oxide-2,2-dimethyl-penam-3-carboxylic acid was dissolved in 200 ml of N,N-dimethylformamide, and a solution of 6.0 g of diethyl phosphoryl cyanide in 45 ml of N,N-dimethylformamide was added dropwise at 0° C. After the addition, 6 g of N-aminopiperidine hydrochloride was added. After 15 minutes, a solution of 8 g of triethylamine in 50 ml of N,N-dimethylformamide was added to the mixture. The mixture was stirred at the same temperature for an additional 30 minutes, and then for 4 hours at room temperature. After standing overnight, the triethylamine hydrochloride was removed by filtration, and N,N-dimethylformamide was distilled off at reduced pressure from the filtrate. The residue was dissolved in ethyl acetate, and extracted with a 1N hydrochloric acid solution. A saturated sodium bicarbonate solution was added to the hydrochloric acid phase to render it alkaline, and the mixture was extracted with ethyl acetate. The ethyl acetate layer was dried, and ethyl acetate was distilled off at reduced pressure to afford 7.4 g of a residue.

The residue exhibited a single peak by thin-layer chromatography with an FID detector (see Example 21), and the δ values (ppm) in its NMR spectrum (CDCl$_3$ solution) were as follows:
1.30 (3H, s),
1.80 (6H, bs),
2.80 (4H, bs),
4.60 (2H, s),
5.20 (1H, m),
6.10 (1H, m),
7.0 - 7.6 (5H, m).

From the above results, this product was determined to be 6β-phenoxyacetamido-1-oxide-2,2-dimethyl-penam-3-carbo-N',N'-1',5'-pentamethylene hydrazide.

(2) Preparation of 7β-phenoxyacetamido-3-methylene-cepham-4-carbo-N',N'-1',5'-pentamethylene hydrazide:

10 g of 6β-phenoxyacetamido-1-oxide-2,2-dimethyl-penam-3-carbo-N',N'-1',5'-pentamethylene hydrazide was dissolved in a mixture of 25 ml of N,N-dimethylacetamide and 25 ml of benzene, and 0.1 g of methanesulfonic acid was added. The mixture was heated for 2 hours at a bath temperature of 110° C. After cooling, 50 ml of ethyl acetate was added to the reaction mixture, and the mixture was washed four times with water, and then dried over anhydrous sodium sulfate. The solvent was distilled off, and the residue was chromatographed on silica gel to afford 7β-phenoxyacetamido-3-methylene-cepham-4-carbo-N',N'-1',5'-pentamethylene hydrazide having the following characterstics.

NMR spectrum, δ (ppm):

1.20 – 2.00 (6H, m),
3.13, 3.95 (2H, AB-q, J=14Hz),
4.56 (2H,s),
5.25 (2H, m),
5.65 – 5.85 (3H, m),
6.68 (1H, bs),
6.80 – 7.50 (6H, m).
IR spectrum, $\nu_{max}^{KBr}$ (Cm$^{-1}$): 3380, 3250, 1765, 1690, 1665.
Mass spectrum, (m/e): 430 (M$^+$).

EXAMPLE 6

Preparation of 7β-phenoxyacetamido-3-methylene-cepham-4-carbo-N,N'-dicyclohexyl hydrazide:

1.013 g of 6β-phenoxyacetamido-1-oxide-2,2-dimethyl -penam-3-carbo-N,N'-dicyclohexyl hydrazine was dissolved in 25 ml of N,N-dimethylacetamide and 25 ml of benzene, and 64 mg of d-10-camphorsulfonic acid was added. The mixture was heated for 1.5 hours at 110° C. After cooling, 50 ml of ethyl acetate was added to the reaction mixture. The mixture was washed four times with water, and dried over anhydrous sodium sulfate. The solvent was distilled off, and the oily residue was purified by preparative silica gel thin-layer chromatography to afford 150 mg of 7β-phenoxyacetamido-3-methylene-cepham-4-carbo-N,N'-dicyclohexyl hydrazide having the following characteristics.

NMR spectrum, δ (ppm):
1.20 – 2.25 (10H, bm),
2.50 (2H, bs),
3.15, 4.07 (2H, AB-q, J=14Hz),
4.52 (2H, s),
5.02 – 5.18 (2H, bd),
5.05 – 5.78 (3H, m),
6.75 – 7.50 (6H, bm).
IR spectrum, $\nu_{max}^{nujol}$ (cm$^{-1}$): 3250, 1750, 1680, 1630.
Mass spectrum, (m/e): 556 (M$^+$).

EXAMPLE 7

Preparation of 7β-phenoxyacetamido-3-methylene-cepham-4-carbo-N,N'-di-n-propyl hydrazide:

1.130 g of 6β-phenoxyacetamido-1-oxide-2,2-dimethyl-penam-3-carbo-N,N'-di-n-propyl hydrazide was dissolved in a mixture of 35 ml of N,N-dimethylacetamide and 35 ml of benzene, and 110 mg of d-10-camphorsulfonic acid was added. The mixture was heated with stirring for 1.5 hours at a bath temperature of 120° C. During the reaction, the low boiling solvent was gradually distilled off, and the by-product water was removed gradually as an azeotrope. After cooling, 400 ml of ethyl acetate was added. The mixture was washed successively with a saturated aqueous solution of sodium bicarbonate, water (five times), and then a saturated aqueous solution of sodium chloride, and then dried over anhydrous sodium sulfate. The solvent was distilled off at reduced pressure to afford 1.09 g of a yellowish foam. The product was chromatographed over silica gel with chloroform as eluant to afford 344 mg of 7β-phenoxyacetamido-3-methylene-cepham-4-carbo-N,N'-di-n-propyl hydrazide as a colorless foam which had the following characteristics.

NMR spectrum (CDCl$_3$), δ (ppm):
0.70 – 1.20 (6H, m),
1.20 – 1.96 (4H, m),
2.63 – 4.10 (7H, m),
4.55 (2H, s), 5.12 – 5.40 (2H, d),
5.56 – 5.87 (2H, m),
6.19 (1H, s),
6.83 – 7.70 (6H, m).
IR spectrum, ν max (CHCl$_3$) (cm$^{-1}$): 3380, 1760, 1685, 1650.
Mass spectrum, (m/e): 446 (M$^+$).

EXAMPLE 8

1.0 g of 6β-phenoxyacetamido-1-oxide-2,2-dimethyl-penam-3-carbo-N,N'-diisopropyl hydrazide was dissolved in a mixture of 25 ml of N,N-dimethylacetamide and 25 ml of benzene, and 100 mg of d-10-camphorsulfonic acid was added. The mixture was heated for 2 hours at a bath temperature of 110° C. During the reaction, the low boiling solvent was gradually distilled off, and the by-product water was gradually removed as an azeotrope. After the reaction, the reaction mixture was worked up and chromatographed in the same way as in Example 1, (2) to afford 550 mg of 7β-phenoxyacetamido-3-methylene-cepham-4-carbo-N,N'-diisopropyl hydrazide.

EXAMPLE 9

0.5 g of 6β-phenoxyacetamido-1-oxide-2,2-dimethyl-penam-3-carbo-N,N'-diisopropyl hydrazide was dissolved in 50 ml of dry dioxane and 170 mg of a pyridinium salt of phenyl phosphoric acid. The mixture was heated under reflux for 7 hours at a bath temperature of 120° C. After cooling, the mixture was worked up and chromatographed in the same way as in Example 1, (2) to afford about 100 mg of 7β-phenoxyacetamido-3-methylene-cepham-4-carbo-N,N'-diisopropyl hydrazide.

EXAMPLE 10

0.5 g of 6β-phenoxyacetamido-1-oxide-2,2-dimethyl-penam-3-carbo-N,N'-diisopropyl hydrazide was dissolved in 50 ml of dioxane. 100 mg of phenylphosphoric acid was added to the mixture, and the resulting mixture was heated under reflux for 10 hours at a bath temperature of 120° C. After cooling, the reaction mixture was worked up and chromatographed in the same way as in Example 1, (2) to afford about 100 mg of 7β-phenoxyacetamido-3-methylene-cepham-4-carbo-N,N'-diisopropyl hydrazide.

EXAMPLE 11

0.5 g of 6β-phenoxyacetamido-1-oxide-2,2-dimethyl-penam-3-carbo-N,N'-diisopropyl hydrazide was dissolved in a mixture of 10 ml of N,N-dimethylacetamide and 10 ml of benzene, and 197 mg of diethyl phosphoryl cyanide was added. The mixture was heated at a bath temperature of 150° C for 4.5 hours while distilling off a low-boiling fraction gradually. After cooling, 100 ml of ethyl acetate was added to the reaction mixture. The mixture was washed five times with water and then dried over anhydrous sodium sulfate. The solvent was distilled off, and the residue was chromatographed on silica gel to afford 7β-phenylacetamido- 3-methylene-cepham-4-carbo-N,N'-diisopropyl hydrazide.

EXAMPLE 12

1.0 g of 6β-phenylacetamido-1-oxide-2,2-dimethyl -penam-3-carbo-N,N'-diisopropyl hydrazide was dissolved in a mixture of 25 ml of N,N-dimethylacetamide and 25 ml of benzene, and 0.1 g of d-10-camphorsulfonic acid was added. The mixture was heated for 2 hours at a bath temperature of 110° C. After cooling, the reaction mixture was worked up and chromatographed in the same way as in Example 2, (2) to afford 0.3 g of 7β-phenylacetamido-3-methylene-cepham- 4-carbo-N,N'-diisopropyl hydrazide.

EXAMPLE 13

1.0 g of 6β-phenoxyacetamido-1-oxide-2,2-dimethyl-penam-3-carbo-N'-p-methoxyphenyl hydrazide was dissolved in a mixture of 25 ml of N,N-dimethylacetamide and 25 ml of benzene, and 0.2 g of methanesulfonic acid was added. The mixture was heated for 5 hours at a bath temperature of 110° C. After cooling, the reaction mixture was worked up and chromatographed in the same way as in Example 3, (2) to afford 7β-phenoxyacetamido-3-methylene-cepham-4-carbo-N'-p-methoxyphenyl hydrazide.

EXAMPLE 14

400 mg of 6β-phenoxyacetamido-1-oxide-2,2-dimethyl-penam-3-carbo-N,N'-dicyclohexyl hydrazide was dissolved in a mixture of 10 ml of N,N-dimethylacetamide and 10 ml of benzene, and 170 mg of diethyl phosphoryl cyanide was added. The mixture was heated for 2 hours at a bath temperature of 110° C. After cooling, the reaction mixture was worked up and purified in the same way as in Example 6 to afford 100 mg of 7β-phenoxyacetamido-3-methylene-cepham-4-carbo-N,N'-dicyclohexyl hydrazide.

EXAMPLE 15

1.0 g of 6β-phenoxyacetamido-1-oxide-2,2-dimethyl-penam-3-carbo-N,N'-dicyclohexyl hydrazide was dissolved in 25 ml of dioxane, and 0.1 g of phenylphosphoric acid was added. The mixture was heated under reflux for 5 hours. After cooling, 100 ml of ethyl acetate was added, and the mixture was washed with water, and then dried over anhydrous sodium sulfate. The solvent was distilled off, and the residue was chromatographed on silica gel to afford 0.2 g of 7β-phenoxyacetamido-3-methylene-cepham-4-carbo-N,N'-dicyclohexyl hydrazide.

EXAMPLE 16

1.0 g of 6β-phenoxyacetamido-1-oxide-2,2-dimethyl-penam-3-carbo-N,N'-dicyclohexyl hydrazide was dissolved in a mixture of 25 ml of N,N-dimethylacetamide and 25 ml of benzene, and 0.2 g of methanesulfonic acid was added. The mixture was refluxed for 2 hours at a bath temperature of 110° C. After cooling, the reaction mixture was worked up and purified in the same way as in Example 6 to afford 7β-phenoxyacetamido-3-methylene-cepham-4-carbo-N,N'-dicyclohexyl hydrazide.

EXAMPLE 17

500 mg of 6β-phenoxyacetamido-1-oxide-2,2-dimethyl-penam-3-carbo-N',N'-3'-oxo-1',5'-tetramethylene hydrazide was dissolved in a mixture of 10 ml of N,N-dimethylacetamide and 10 ml of benzene, and 50 mg of d-10-camphorsulfonic acid was added. The mixture was heated for 3 hours at a bath temperature of 120° C. After cooling, 100 ml of chloroform was added, and the mixture was washed four times with water, and dried over anhydrous sodium sulfate. The solvent was distilled off to afford a yellow residue. Chromatography of the residue over silica gel afforded 7β-phenoxyacetamido-3-methylene-cepham-4-carbo-N',N'-3'-oxo-1',5'-tetramethylene hydrazide.

EXAMPLE 18

450 mg of 6β-phenoxyacetamido-1-oxide-2,2-dimethyl-penam-3-carbon-N',N'-3'-oxo-1',5'-tetramethylene hydrazide was dissolved in a mixture of 10 ml of N,N-dimethylacetamide and 10 ml of benzene, and 196 mg of diethyl phosphoryl cyanide was added. The mixture was reacted for 3 hours at a bath temperature of 120° C. After cooling, 50 ml of chloroform was added, and the mixture was washed three times with water and then dried over anhydrous sodium sulfate. The solvent was distilled off to afford a yellowish brown residue. Chromatography of the residue over silica gel afforded 7β-phenoxyacetamido-3-methylene-cepham-4-carbo-N',N'-3'-oxo-1',5'-tetramethylene hydrazide.

EXAMPLE 19

1.0 g of 6β-phenoxyacetamido-1-oxide-2,2-dimethyl-penam-3-carbo-N',N'-1',5'-pentamethylene hydrazide was dissolved in a mixture of 25 ml of N,N-dimethylacetamide and 25 ml of benzene, and 0.1 g of d-10-camphorsulfonic acid was added. The mixture was heated for 3 hours at a bath temperature of 100° C. After cooling, the reaction mixture was worked up and chromatographed in the same way as in Example 5, (2) to afford 0.55 g of 7β-phenoxyacetamide-3-methylene-cepham-4-carbo-N',N'-1',5'-pentamethylene hydrazide.

EXAMPLE 20

450 mg of 6β-phenoxyacetamido-1-oxide-2,2-dimethyl-penam-3-carbo-N',N'-1',5'-pentamethylene hydrazide was dissolved in a mixture of 10 ml of N,N-dimethylacetamide and 10 ml of benzene, and 190 mg of diethyl phosphoryl cyanide was added. The mixture was heated for 3 hours at a bath temperature of 120° C. After cooling, 50 ml of chloroform was added to this mixture, and the resulting mixture was washed with water, and dried over anhydrous sodium sulfate. The solvent was distilled off to afford a yellowish brown residue. Chromatography of the residue on silica gel afforded 7β-phenoxyacetamido-3-methylene-cepham-4-carbo-N',N'-1',5'-tetramethylene hydrazide.

EXAMPLE 21

1.0 g of 6β-phenoxyacetamido-1-oxide-2,2-dimethylene penam-3-carbo-N,N'-diisopropyl hydrazide was dissolved in 50 ml of dioxane, and 100 mg of d-10-camphorsulfonic acid and 0.18 ml of pyridine were added. The mixture was refluxed for 2 hours. The solvent was dehydrated by inserting a column packed with anhydrous magnesium sulfate into a path of refluxing. After the reaction, a greater part of the solvent was distilled off at reduced pressure, and 100 ml of ethyl acetate was added. The mixture was washed with water, and dried. The reaction products were chromatographed (TLC) on a silica gel stick developed with a mixture of chloroform and diethyl ether, and quantitatively analyzed by thinchrograph. The thinchrograph used was Thinchrograph TFG-10, a product of Iatron Laboratory Inc. (By this technique, chromatography is performed on a silica gel sintered stick, which is quantitatively analyzed by a flame ionization detector. See, for example,: JAPAN ANALYST Vol. 22, pp. 980–987 (1973)).

It was found that 7β-phenoxyacetamido-3-methylene-cepham- 4-carbo-N,N'-diisopropyl hydrazide was obtained in a yield of 51%.

EXAMPLE 22

2.0 g of 6β-phenylacetamido-1-oxide-2,2-dimethyl-penam-3-carbo-N,N'-diisopropyl hydrazide was dissolved in 80 ml of dioxane, and 200 mg of d-10-camphorsulfonic acid and 0.06 ml of pyridine were added. While dehydrating the solvent, the mixture was heated under reflux for 2 hours. The resulting reaction mixture was treated in the same way as in Example 21 to afford 0.63 g of 7β-phenylacetamido-3-methylene-cepham-4-carbo-N,N'-diisopropyl hydrazide.

EXAMPLE 23

5.0 g of 6β-phenylacetamido-1-oxide-2,2-dimethyl-penam-3-carbo-N,N'-diisopropyl hydrazide was dissolved in 200 ml of dioxane, and 500 mg of d-10-camphorsulfonic acid and 0.90 ml of pyridine were added. The mixture was refluxed for about 2 hours while dehydrating the solvent in the same way as in Example 21. Quantitative analysis of the products in the same way as in Example 21 showed that 7β-phenylacetamido-3-methylene-cepham-4-carbo-N,N'-diisopropyl hydrazide was obtained in a yield of 53%.

EXAMPLE 24

2.0 g of 6β-phenylacetamido-1-oxide-2,2-dimethyl-penam-3-carbo-N,N'-diisopropyl hydrazide was dissolved in 80 ml of dioxane, and 0.1 ml of methanesulfonic acid and 0.13 ml of pyridine were added. The mixture was refluxed for 1.5 hours while dehydrating the solvent in the same way as in Example 21. Quantitative analysis of the reaction products in the same way as in Example 21 showed that 7β-phenylacetamido-3-methylene-cepham-4-carbo-N,N'-diisopropyl hydrazide was obtained in a yield of 25%.

EXAMPLE 25

2.0 g of 6β-phenylacetamido-1-oxide-2,2-dimethyl-penam-3-carbo-N,N'-diisopropyl hydrazide was dissolved in 80 ml of dioxane, and 0.09 ml of methanesulfonic acid and 0.40 ml of α-picoline were added. The mixture was refluxed for 1.5 hours in the same way as in Example 21. Quantitative analysis of the reaction products showed that 7β-phenylacetamido-3-methylene-cepham-4-carbo-N,N'-diisopropyl hydrazide was obtained in a yield of 36%.

EXAMPLE 26

2.0 g of 6β-phenylacetamido-1-oxide-2,2-dimethyl-penam-3-carbo-N,N'-diisopropyl hydrazide was dissolved in 80 ml of dioxane, and 170 mg of benzenesulfonic acid and 0.36 ml of pyridine were added. The mixture was refluxed for 2.5 hours in the same way as in Example 21. Quantitative analysis of the reaction products showed that 7β-phenylacetamido-3-methylene-cepham-4-carbo-N,N'-diisopropyl hydrazide was obtained in a yield of 32%.

EXAMPLE 27

2.0 g of 6β-phenylacetamido-1-oxide-2,2-dimethyl-penam-3-carbo-N,N'-diisopropyl hydrazide was dissolved in 80 ml of methyl isobutyl ketone, and 0.2 g of d-10-camphorsulfonic acid and 0.34 ml of pyridine were added. The mixture was refluxed for 3 hours in the same way as in Example 21. Quantitative analysis of the reaction products showed that 7β-phenylacetamido-3-methylene-cepham-4-carbo-N,N'-diisopropyl hydrazide was obtained in a yield of 26%.

EXAMPLE 28

2.0 g of 6β-phenylacetamido-1-oxide-2,2-dimethyl-penam-3-carbo-N,N'-diisopropyl hydrazide was dissolved in 80 ml of dioxane, and 0.2 g of d-10-camphorsulfonic acid and 0.40 ml of α-picoline were added. The mixture was refluxed for 2 hours in the same way as in Example 21. Quantitative analysis of the reaction products in the same way as in Example 21 showed that 7β-phenylacetamido-3-methylene-cepham-4-carbo-N,N'-diisopropyl hydrazide was obtained in a yield of 39%.

EXAMPLE 29

2.0 g of 6β-phenylacetamido-1-oxide-2,2-dimethyl-penam-3-carbo-N,N'-diisopropyl hydrazide was dissolved in 100 ml of dioxane, and 250 mg of d-10-camphorsulfonic acid and 0.36 ml of 2,3-lutidine were added. The mixture was refluxed for 1.5 hours in the same way as in Example 21. Quantitative analysis of the reaction products showed that 7β-phenylacetamido-3-methylene-cepham-4-carbo-N,N'-diisopropyl hydrazide was obtained in a yield of 46%.

EXAMPLE 30

2.0 g of 6β-phenoxyacetamido-1-oxide-2,2-dimethyl-penam-3-carbo-N,N'-dicyclohexyl hydrazide was dissolved in 80 ml of dioxane, and 0.2 g of d-10-camphorsulfonic acid and 0.32 ml of pyridine were added. The mixture was refluxed for 2 hours in the same way as in Example 21. Quantitative analysis of the reaction products in the same way as in Example 21 showed that 7β-phenoxyacetamido-3-methylene-cepham-4-carbo-N,N'-dicyclohexyl hydrazide was obtained in a yield of 35%.

Control 1

500 mg of 6β-phenylacetamido-1-oxide-2,2-dimethyl-penam-3-carbo-N,N'-diisopropyl hydrazide was added to 8 ml of dry dioxane containing 8.0 mg of pyridine and 11.2 mg of orthophosphoric acid. The mixture was heated under reflux for 18 hours in a stream of nitrogen. The solvent was distilled off at reduced pressure from the reaction mixture. Preparative thin-layer chromatography of the residue on silica gel plates (thickness 0.5 mm; size 20 cm × 20 cm) developed with a mixture of benzene and ethyl acetate in a volume ratio of 1:1 as a developing solvent afforded 250 mg of the starting 6β-phenylacetamido-1-oxide-2,2-dimethyl-penam-3-carbo-N,N'-diisopropyl hydrazide and 50 mg of 7β-phenylacetamido-3-methyl-3-cephem-4-carbo-N,N'-diisopropyl hydrazide as a product. In addition, two other bands were present on the thin-layer chromatographic plate. Products corresponding to these two bands were obtained in an amount of 110 mg and 50 mg, respectively. These two products were developed with a mixture of benzene and ethyl acetate in a volume ratio of 1:1 on a silica gel thin-layer chromatographic plate, and found to be pure substances. However, in the NMR spectra (in $CDCl_3$) of these products, a resonance signal ($\delta = 5.55 - 5.75$) of the 3-position methylene group of the corresponding 3-methylene-cepham-4-carbohydrazide derivative was not observed. Hence, it was ascertained that 7β-phenylacetamido-3-methylene-cepham-4-carbo-N,N'-diisopropyl hydrazide was not formed.

What we claim is:

1. A process for preparing a compound of the formula

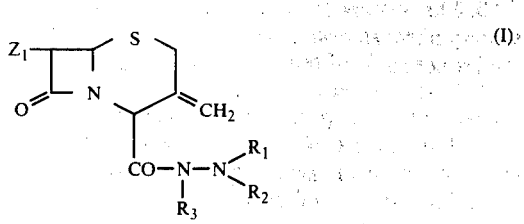

wherein $R_1$ represents alkyl containing 3 to 8 carbon atoms, cycloalkyl containing 5 to 8 carbon atoms, phenyl or phenyl substituted by alkyl containing 1 to 4 carbon atoms or alkoxy containing 1 to 4 carbon atoms, and one of $R_2$ and $R_3$ represents hydrogen and the other represents hydrogen, alkyl containing 3 to 8 carbon atoms, cycloalkyl containing 5 to 8 carbon atoms, phenyl or phenyl substituted by alkyl containing 1 to 4 carbon atoms or alkoxy containing 1 to 4 carbon atoms or alkoxy containing 1 to 4 carbon atoms; $R_1$ and $R_2$ form, together with the nitrogen atom to which they are attached, a 5- or 6-membered heterocyclic ring which may contain one oxygen atom as a further hetero atom, and $R_3$ represents hydrogen, and $Z_1$ represents amino or amino protected by an amino-protecting group which can be removed without cleaving the β-lactam moiety of the cepham ring, or an acid addition salt of said compound, which comprises heating a compound of the formula

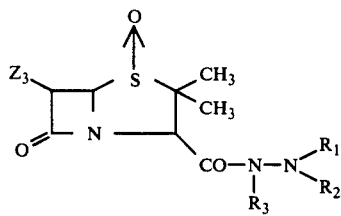

wherein $R_1$, $R_2$ and $R_3$ are the same as defined above, and $Z_3$ is amino protected by an amino-protecting group which can be removed without cleaving the β-lactam moiety of the penam ring, to a temperature of at least 50° C in the presence of a rearrangement promoter selected from the group consisting of (a) an organic sulfonic acid of the formula $$R_{12}(SO_3H)_n$$

wherein $R_{12}$ represents a hydrocarbon residue containing 1 to 15 carbon atoms and having a valence of n, which may contain at least one hetero atom selected from nitrogen, oxygen, sulfur and halogen, and n is an integer of 1 to 3, (b) a mono- or di-ester of phosphoric acid of the formula

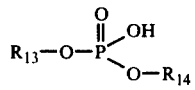

wherein $R_{13}$ represents a monovalent hydrocarbon residue containing 1 to 12 carbon atoms and optionally containing at least one hetero atom selected from nitrogen, oxygen, sulfur and halogen, and $R_{14}$ represents hydrogen or a monovalent hydrocarbon residue containing 1 to 12 carbon atoms and optionally containing at least one hetero atom selected from nitrogen, oxygen, sulfur and halogen, (c) an organic phosphonic acid or monoester thereof of the formula

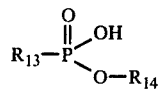

wherein $R_{13}$ and $R_{14}$ are the same as defined above, and (d) a diester of a phosphoryl cyanide or azide of the formula

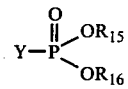

wherein $R_{15}$ and $R_{16}$, independently of each other, represent alkyl containing 1 to 5 carbon atoms, aryl containing 6 to 10 carbon atoms or aralkyl containing 7 to 12 carbon atoms, and Y is —CN or —$N_3$, and, if desired, subjecting the resulting product to a reaction of eliminating the amino-protecting group, and, if desired, subjecting the reaction product to an acid addition salt-forming reaction.

2. The process of claim 1 wherein the rearrangement promoter is selected from the group consisting of said promoters (a), (b) and (c) as defined in claim 1, and the amount of the promoter is 0.05 to 1.5 moles per mole of the compound of formula (II).

3. The process of claim 1 wherein the rearrangement promoter is said promoter (d) as defined in claim 1, and the amount of the promoter is 0.8 to 5 moles per mole of the compound of formula (II).

4. The process of claim 1 wherein the heating is carried out in the co-presence of a tertiary nitrogen-containing cyclic compound selected from the group consisting of pyridine, 2-ethyl pyridine, 3-ethyl pyridine, 4-ethyl pyridine, 5-ethyl-2-methyl pyridine, 2-methoxy pyridine, 4-methoxy pyridine, 3-methoxy pyridine, 2-chloropyridine, 4-chloropyridine, 2-methyl-3-chloropyridine, 3-nitropyridine, 4-nitropyridine, α-picoline, β-picoline, γ-picoline, 2,3-lutidine, 2,6-lutidine, pyrimidine and quinoline.

5. The process of claim 1 wherein, in formula (I), $R_1$ represents alkyl containing 3 to 6 carbon atoms, cycloalkyl containing 5 to 7 carbon atoms, phenyl or phenyl substituted by alkyl containing 1 to 4 carbon atoms or alkoxy containing 1 to 4 carbon atoms, and one of $R_2$ and $R_3$ represents hydrogen and the other represents hydrogen, alkyl containing 3 to 6 carbon atoms, cycloalkyl containing 5 to 7 carbon atoms, phenyl or phenyl substituted by alkyl containing 1 to 4 carbon atoms or alkoxy containing 1 to 4 carbon atoms; or $R_1$ and $R_2$ form, together with the nitrogen atom to which they are attached, a 5- or 6-membered heterocyclic ring which may contain one oxygen atom as a further hetero atom, and $R_3$ represents hydrogen, and $Z_1$ represents amino, phenylacetamido, phenoxyacetamido or phthalimido, and, in formula (II), $Z_3$ represents phenylacetamido, phenoxyacetamido or phthalimido.

6. The process of claim 1 wherein the heating is carried out to provide a reaction temperature of 60 to 170° C.

7. The process of claim 1 wherein the amount of the rearrangement promoter is at least 0.01 mole per mole of the compound of formula (II).

8. The process of claim 1 wherein the amount of the rearrangement promoter is 0.05 to 5 moles per mole of the compound of formula (II).

9. The process of claim 1 wherein the rearrangement promoter is methanesulfonic acid, d-10-camphorsulfonic acid, or p-toluenesulfonic acid.

10. The process of claim 4 wherein the amount of the tertiary nitrogen-containing cyclic compound is 0.5 to 2 moles per mole of the rearrangement promoter.

11. The process of claim 1 wherein the heating is carried out in an aprotic organic solvent.

12. The process of claim 11 wherein the aprotic organic solvent is an aprotic polar organic solvent.

13. The process of claim 1 wherein the heating is carried out while removing water, generated during the reaction from the reaction system.

* * * * *